(12) United States Patent
Hell et al.

(10) Patent No.: US 6,709,156 B1
(45) Date of Patent: Mar. 23, 2004

(54) COOLING DEVICE AND COMPUTED TOMOGRAPHY APPARATUS EMPLOYING SAME

(75) Inventors: Erich Hell, Erlangen (DE); Detlef Mattern, Erlangen (DE); Peter Schardt, Hoechstadt (DE)

(73) Assignee: Siemens Aktiengesellschaft, München (DE)

( * ) Notice: Subject to any disclaimer, the term of this patent is extended or adjusted under 35 U.S.C. 154(b) by 5 days.

(21) Appl. No.: 09/664,338

(22) Filed: Sep. 18, 2000

(30) Foreign Application Priority Data

Sep. 22, 1999 (DE) .......................................... 199 45 413

(51) Int. Cl.⁷ ............................................... H01J 35/10
(52) U.S. Cl. ...................................... 378/199; 378/200
(58) Field of Search ................................. 378/199, 200, 378/4, 15

(56) References Cited

U.S. PATENT DOCUMENTS

| | | | |
|---|---|---|---|
| 4,115,697 A | | 9/1978 | Hounsfield et al. |
| 4,593,261 A | | 6/1986 | Forster et al. |
| 4,866,743 A | * | 9/1989 | Kroener .......................... 378/4 |
| 5,012,505 A | | 4/1991 | Zupancic et al. |
| 5,299,249 A | * | 3/1994 | Burke et al. ................... 378/15 |
| 5,313,512 A | * | 5/1994 | Tanaka ......................... 378/200 |
| 5,610,968 A | * | 3/1997 | Deucher et al. ............ 378/199 |
| 5,761,269 A | | 6/1998 | Sugihara et al. |
| 6,095,684 A | * | 8/2000 | Sribar et al. ................. 378/193 |

FOREIGN PATENT DOCUMENTS

DE    OS 197 04 338    8/1998

* cited by examiner

*Primary Examiner*—David V. Bruce
*Assistant Examiner*—Chin-Cheng Glen Kao
(74) *Attorney, Agent, or Firm*—Schiff Hardin & Waite

(57) ABSTRACT

A cooling device for an X-ray source arranged at a gantry rotatable around a rotational axis has a ring-like heat exchanger that is arranged at the gantry and is thermally conductively connected to the X-ray source. The cooling device is useable in a computed tomography apparatus having the X-ray source.

12 Claims, 3 Drawing Sheets

COOLING DEVICE AND COMPUTED TOMOGRAPHY APPARATUS EMPLOYING SAME

BACKGROUND OF THE INVENTION

1. Field of the Invention

The present invention is directed to a cooling device for an X-ray source arranged at a gantry rotatable around a rotational axis, as well as to a computed tomography apparatus with such a cooling device.

2. Description of the Prior Art

Approximately 99% of the electrical energy utilized in the generation of X-rays with an X-ray source is converted into thermal energy. The heat arising in the operation of the X-ray source usually must be eliminated from the X-ray source in some manner in order to be able to operate the X-ray source over a longer time span for radiological exposures of a subject. This is particularly required when high X-ray power is needed as, for example, in computed tomography or angiography.

Added thereto as a complicating factor in computed tomography is that the X-ray source is arranged at a gantry that rotates around a rotational axis during radiological exposures. Whereas electrical energy can be supplied to the X-ray source relatively simply via wiper rings, the elimination of the heat arising during operation of the X-ray source proves problematical. X-ray sources with a rotating anode X-ray tube that are conventionally utilized in computer tomography and operate so that the heat arising during operation of the rotating anode X-ray tube is intermediately stored in the anode dish and is transferred—mainly by thermal radiation—to a coolant and insulating oil that surrounds the rotating anode X-ray tube and is contained in a housing of the X-ray radiator. The coolant and insulating oil usually circulates in a closed circulation loop through the housing of the X-ray radiator and a first heat exchanger that co-rotates with the gantry that emits the heat to the air surrounding the gantry. A second heat exchanger, that is stationary relative to the gantry, cools the heated air around the gantry and transfers the heat absorbed from the air to, for example, a stationary cooling water system.

A disadvantage of such an arrangement for cooling the rotating anode X-ray tube is that the majority of the heat transmission from the first heat exchanger to the air surrounding the gantry as well as the majority of the heat transmission from the air to the second heat exchanger takes place in a significantly locally limited manner, i.e. only to the environment of the respective locations of the X-ray source or the first heat exchanger, so that the effective area for the heat exchange is relatively small.

SUMMARY OF THE INVENTION

An object of the present invention is to implement a cooling arrangement of the type initially described wherein the elimination of heat generated during operation by an X-ray source arranged at a gantry is improved. A further object of the invention is to provide a computed tomography apparatus having an X-ray source wherein the heat generated during operation by the X-ray source arranged at a gantry is eliminated in an improved manner.

This object is inventively achieved by a cooling arrangement for an X-ray source arranged at a gantry that is rotatable around a rotational axis, the cooling arrangement having a ring-like heat exchanger that is arranged at the gantry and is connected to the X-ray source in thermally conductive fashion. The ring-like fashioning of the heat exchanger, i.e. the fashioning thereof adapted to the preferred form of the gantry, enables a large-area heat transfer of the heat arising when generating X-rays with the X-ray source from the heat exchanger to the air surrounding the heat exchanger in a simple way, with heat transfer occurring over the entire circumferential surface of the ring-like heat exchanger. Although the heat transfer from the X-ray source to the heat exchanger is still relatively locally limited, the area for the heat transfer from the heat exchanger to the air surrounding the heat exchanger is enlarged so that the elimination of the heat is significantly improved. Whereas the area for the heat exchange for current, standard heat exchangers provided at the gantry amounts to approximately $0.1\ m^2$, three times the area for the heat exchanger is already obtained with the inventive ring-like, heat exchanger adapted to the size of the gantry that has a radius of approximately 0.5 m and a width of approximately 0.1 m. The heat exchanger is preferably arranged ring-like around the gantry, however, the heat exchanger alternatively can be arranged axially offset relative to the gantry in the direction of the rotational axis and preferably with substantially the same radius as the gantry.

In a preferred embodiment of the invention the heat exchanger is rotatable around the rotational axis together with the gantry. The heat transfer from the X-ray source to the first heat exchanger therefore can be accomplished in a simple way by thermal conduction since no parts of the gantry and the heat exchanger that move relative to one another and form heat barriers are present.

In a version of the invention the heat exchanger is formed of at least one heat exchange element, or at least two heat exchange elements that are arranged annularly and are connected to one another and to the X-ray source in thermally conductive fashion. This version thus allows the use of individual heat exchange elements that are commercially obtainable and thus economical, of the type, for example, employed in the automotive industry. When arranged ring-like and connected to one another, these heat exchange elements, which are usually cuboid, result in a heat exchanger which effectively eliminates the heat generated during operation of the X-ray source for the X-ray source to the heat exchanger.

A more uniform distribution of the heat generated by the X-ray source and absorbed by the heat exchanger is achieved in a version of the invention wherein a medium flows through the heat exchanger in a closed circulation loop. The medium preferably flows not only through the heat exchange elements connected to one another by, for example, conduits but also flows through cooling and insulating oil that surrounds the X-ray source. This results in a relatively uniform distribution of the heat over the heat exchanger, and thus a large-area heat transfer from the heat exchanger to the air surrounding the heat exchanger. For example, the cooling and insulating oil also can be employed as the flowing medium.

In another version of the invention coverings extending between the heat exchange elements in the circumferential direction connect the heat exchange elements to one another, and/or annular guide devices at both sides of the heat exchanger are provided. These coverings and/or guide elements conduct an air stream produced by rotation of the heat exchanger, and heated at the heat exchanger, toward the exterior away from the gantry. In this way, heated air is prevented from proceeding into the interior of the gantry which could negatively influence the functioning of the radiation detector (usually arranged at the gantry) and its appertaining electronics.

In another preferred embodiment of the invention, the aforementioned heat exchanger serves as first heat exchanger, and a second heat exchanger is provided that interacts with the first heat exchanger, resulting in the elimination of the heat generated by the X-ray source being further improved. In a version of this embodiment, the second heat exchanger is stationary relative to the first heat exchanger, and the second heat exchanger is either annularly arranged around the first heat exchanger or is attached to the first heat exchanger axially offset in the direction of the rotational axis. In all instances, the two heat exchangers preferably reside extremely closely opposite one another, separated only by an air gap, so that—due to this arrangement—the second heat exchanger is charged with only a comparatively slight, secondary stream of air that has not been heated at the first heat exchanger. As a result, a higher temperature difference between the primary side and the secondary side (i.e. the side absorbing the heat and the side emitting the heat, for example to the air surrounding the second heat exchanger), that is directly, proportional to the cooling power is effective at the second heat exchanger.

In another embodiment of the invention, the second heat exchanger also can be formed of one or more heat exchange elements connected to one another, or a medium can flow through the second heat exchanger. Commercially obtainable heat exchange elements also can be employed to form the second heat exchanger to the lower the manufacturing costs. The connection of the heat exchange elements to one another and having a medium flow through the heat exchange elements produce an optimally uniform distribution of the heat over the second heat exchanger—as in the case of the first heat exchanger—and thus resulting in a large-area heat transfer from the second heat exchanger to, for example the air surrounding the second heat exchanger.

In another version of the invention, the second heat exchanger also has coverings extending between the heat exchange elements thereof in the circumferential direction that connect the heat exchange elements to one another. The first and second heat exchangers can have inter-engaging, annular guide devices that guide an air stream generated as a result of the rotation of the first heat exchanger, and heated at the first heat exchanger, to the second heat exchanger. The coverings between the heat exchange elements of the second heat exchanger prevent penetration of the non-heated air into the air gap between the first and second heat exchangers. Additionally, the inter-engaging, annular guide devices cause the air heated at the first heat exchanger to be guided in the direction of the second heat exchanger so that this heated air cannot undesirably proceed into the inside of the gantry and negatively influence the functioning of the radiation detector and its appertaining electronics.

DETAILED DESCRIPTION OF THE PREFERRED EMBODIMENTS

Figure 1:
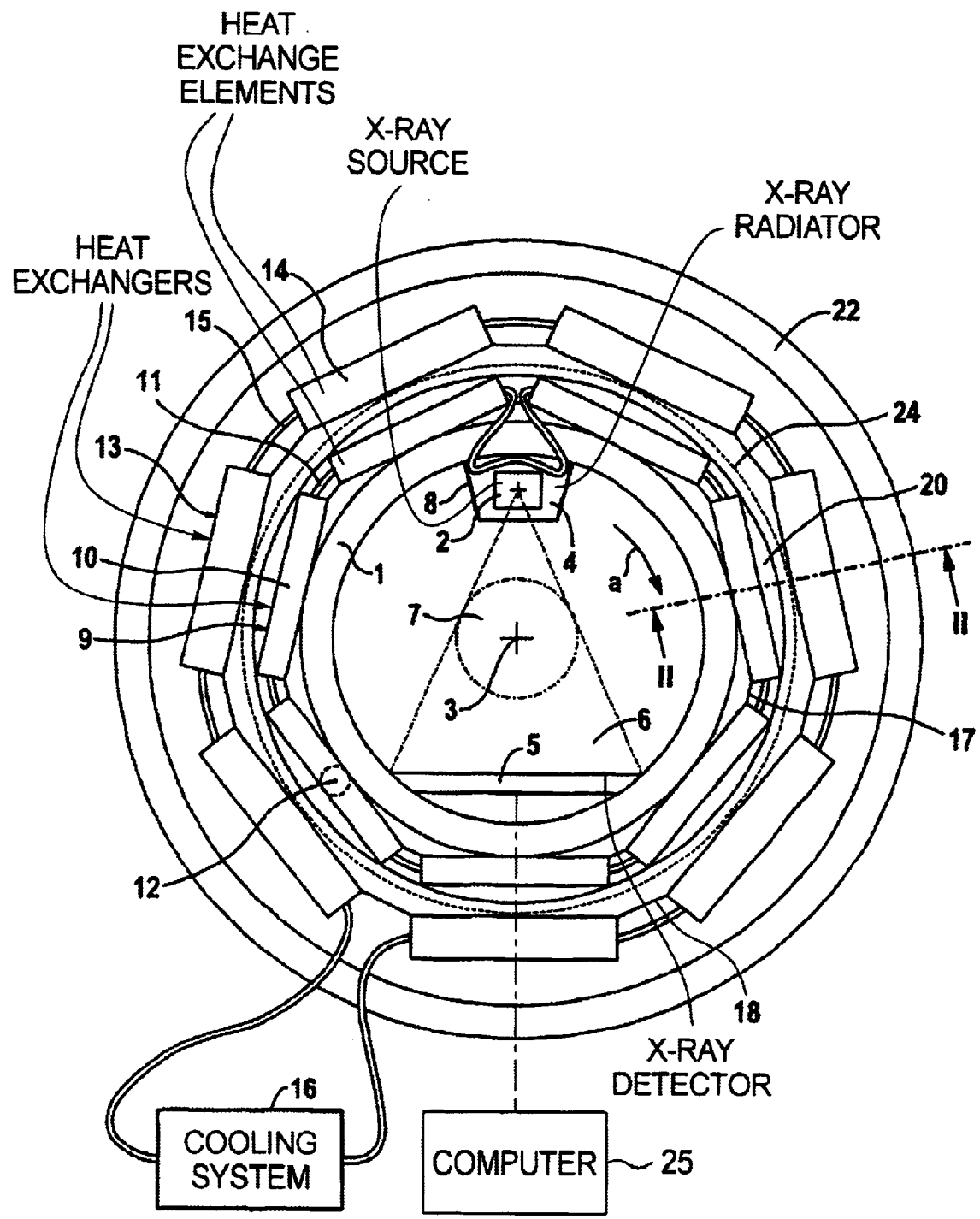
FIG. 1 shows an inventive cooling device with first and second ring-like heat exchangers.

FIG. 1 is a schematic illustration of an inventive cooling arrangement for an X-ray source 2 arranged at an annular gantry 1. In the exemplary embodiment, the gantry 1 is part of a computed tomography apparatus and is seated therein so as to be rotatable in the direction of the arrow 'a' around a rotational axis 3 is perpendicular to the plane of the drawing.

An X-ray radiator 4 that contains the aforementioned X-ray source 2, which can be a rotating bulb tube, and a detector 5 are arranged opposite one another. During operation of the computed tomography apparatus, the gantry 1 rotates around the rotational axis 3, and a fan-shaped X-ray beam 6 emanating from the X-ray source 2 penetrates a measuring field 7 and is incident on the X-ray detector 5. Output signals from the X-ray detector 5 are supplied to a computer 25 which reconstructs an image of a subject (not shown) in the measuring field 7 in a known manner. The electrical connections of the X-ray source 2 and the detector 5 are accomplished via wiper rings in a known way that is not shown. The housing 8 of the X-ray radiator 4 containing the X-ray source 2 is filled (in a way not shown in detail) with cooling and insulating oil in order to cool the rotating bulb tube during operation of the computed tomography apparatus.

In the exemplary embodiment, a first heat exchanger 9, that is fashioned ring-like and is rotatable around the rotational axis 3 together with the gantry 1, is arranged around the gantry 1. In the exemplary embodiment, the heat exchanger 9 is formed of seven annularly arranged heat exchange elements 10 that are filled with a cooling medium and that are connected to one another via hose conduits 11. Such a hose conduit 11 is also conducted through the housing 8, and thus the cooling and insulating oil of the X-radiator 4 as well, in a helical course, for example. A circulating pump 12 schematically indicated in one of the heat exchange elements 10 produces a circulation of the medium through the heat exchange elements 10 and the X-ray radiator 4.

In the exemplary embodiment, a second heat exchanger 13 that interacts with the first heat exchanger 9 and that is likewise fashioned ring-like is arranged around the first heat exchanger 9. The heat exchanger 13 is stationary relative to the heat exchanger 9. An air gap 21 (see FIG. 2) is present between the two heat exchangers 9 and 13. Like the heat exchanger 9, the heat exchanger 13 in the exemplary embodiment also is formed of seven annularly arranged heat exchange elements 14 in which a medium flows, that are connected to one another via hose conduits 15, so that the medium can circulate through the heat exchange elements 14.

In the exemplary embodiment, the medium is additionally conducted via a cooling system 16 that actively cools the medium and contains a circulating pump (not shown) that accomplishes the circulation of the medium through the heat exchange elements 14 and the cooling system 16.

During operation of the computed tomography apparatus, the medium of the heat exchanger 9 absorbs heat from the cooling and insulating oil when it flows through the X-ray radiator 4, and, as a consequence of the circulation of the medium through the heat exchange elements 10, achieves a relatively uniform distribution of the heat over the first heat exchanger 9. In this way, heat transfer from the first heat exchanger 9 to the air that surrounds the heat exchanger 9 and is present in the air gap 21 between the heat exchanger 9 and the heat exchanger 13, ensues in large-area fashion over the entire circumference of the heat exchanger 9. As a result, the elimination of the heat from the rotating bulb tube forming the X-ray source 2 is noticeably improved.

As a result of the rotation of the heat exchanger 9 with the gantry 1, the air heated by the heat exchanger 9 likewise circulates and charges the primary side of the heat exchanger 13 facing toward the heat exchanger 9 that absorbs the heat from the air circulating in the air gap 21. As a result, medium of the heat exchanger 13 flowing through the heat exchange elements 14 is elevated in temperature. The elimination of the heat picked up by the heat exchanger 13 ensues to the air surrounding the heat exchanger 13 and also ensues to the cooling system 16 as a result of the circulation of the medium.

Respective coverings 17 or 18 are provided between the heat exchange elements 10 of the first heat exchanger 9 as well as between the heat exchange elements 14 of the second heat exchanger 13. The coverings 17 prevent heated air from proceeding from the air gap 21 into the inside of the gantry 1, which could cause malfunctioning of the detector 5 as well as its appertaining electronics (not shown in detail). The coverings 18, in contrast, mainly serve to prevent secondary stream of non-heated air from proceeding into the air gap 21 between the heat exchangers 9 and 13. In this way, the temperature difference between primary and secondary sides, i.e. the side of the heat absorption and the side of the heat emission, remains higher, this being directly proportional to the cooling power.

Figure 2:
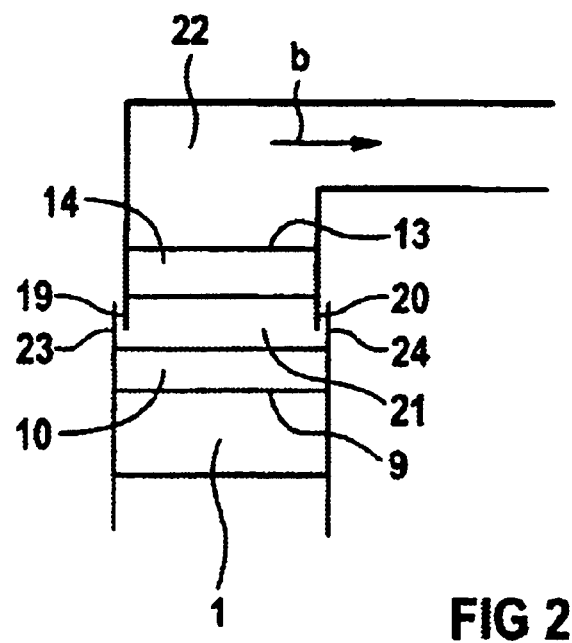
FIG. 2 is a view of the inventive cooling device in the direction of the arrow II from FIG. 1.

FIG. 2 is a view of the cooling arrangement in the direction of the arrow II from FIG. 1. FIG. 2 shows a cross-section through two heat exchange elements 10, 14 of the heat exchangers 9 and 13. As can be seen better in FIG. 2 compared to FIG. 1, each of the first heat exchanger 9 and the second heat exchanger 13 has two annular guide devices 23, 24 and 19, 20, respectively that are arranged at both sides of the heat exchange elements 10 and 14, respectively, and engage into one another. The guide devices prevent the air that is heated as a result of the rotation of the heat exchanger 9 and that circulates in the air gap 21 from proceeding into the inside of the gantry 1 and guide therein from the gantry 1 in the direction toward the second heat exchanger 13. Moreover, the guide devices prevent the penetration of secondary air into the air gap 21. FIG. 2 also shows a device 22—that cannot be clearly seen in FIG. 1—for the air that is heated at the heat exchanger 13 and which surrounds the heat exchanger 13 and that is eliminated in the direction of the arrow 'b'.

In the exemplary embodiment, a second heat exchanger 13 for the elimination of the heat generated during the operation of the X-ray source 2 is provided in addition to the first heat exchanger 9, however, the inventive cooling arrangement need not necessarily include the second heat exchanger 13. If the second heat exchanger 13 is omitted, the first heat exchanger 9 emits the heat absorbed from the X-ray source 2 to the surrounding air during operation of the computed tomography apparatus case. Such an embodiment of a computed tomography apparatus is suitable, for example, for investigating materials in factories wherein high demands as to hygiene are not made.

The above-described embodiment of the heat exchangers 9 and 13 respectively with seven heat exchange elements 10, 14 is only an example. The heat exchanger 9 as well as the heat exchanger 13 can be composed of only a single, annularly closed heat exchange element, of a few or of a multitude of annularly arranged heat exchange elements that, as in the case of the present exemplary embodiment, are fashioned cuboid. The number of heat exchange elements is preferably adapted to the required cooling capacity.

Further, it is not necessarily required that for a medium to flow through the heat exchange elements. The heat exchange elements can merely be connected to one another in thermally conductive fashion, for example via copper conduits. For example, the coverings 17 or 18 of the heat exchangers 9 and 13 can serve as such copper conduits.

In the case of the heat exchanger 9, the medium flowing through the heat exchange elements can, for example, be the cooling and insulating oil of the X-ray radiator 4, so that no additional medium that distributes heat over the heat exchanger is required beyond the cooling and insulating oil.

The first heat exchanger 9, moreover, need not necessarily rotate together with the gantry 1 but can be stationary relative to the gantry 1. In this case, the heat transmission from the X-ray source 2 or the X-radiator 4 to the first heat exchanger 9 ensues, for example, via the air that is present between the X-ray radiator 4 and the first heat exchanger 9 and that is heated at the X-ray radiator 4 and that serves as thermally conductive medium.

In the exemplary embodiment, the heat exchanger 9 is arranged around the gantry 1 and the heat exchanger 13 is arranged around the heat exchanger 9. Alternative arrangements of heat exchangers relative to one another and relative to the gantry 1 are shown in FIGS. 3 and 4.

Figure 3:
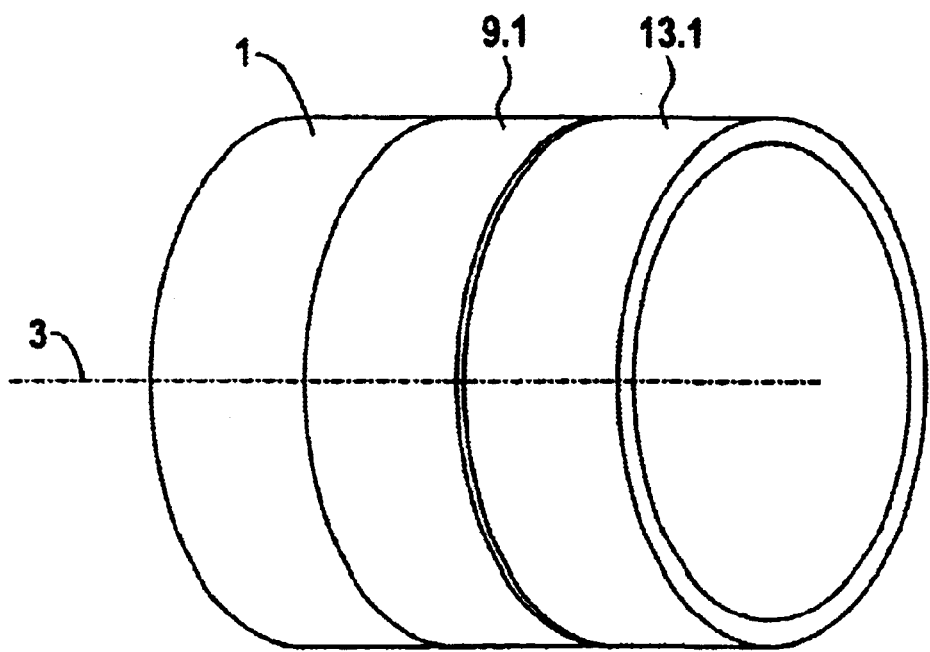
FIGS. 3 and 4 respectively show arrangements of the first and second heat exchangers relative to one another and relative to the gantry.

In FIG. 3, a heat exchanger 9.1 is arranged axially offset in the direction of the rotational axis 3 relative to the gantry 1 and a heat exchanger 13.1 is arranged axially offset in the direction of the rotational axis 3 relative to the heat exchanger 9.1.

Figure 4:
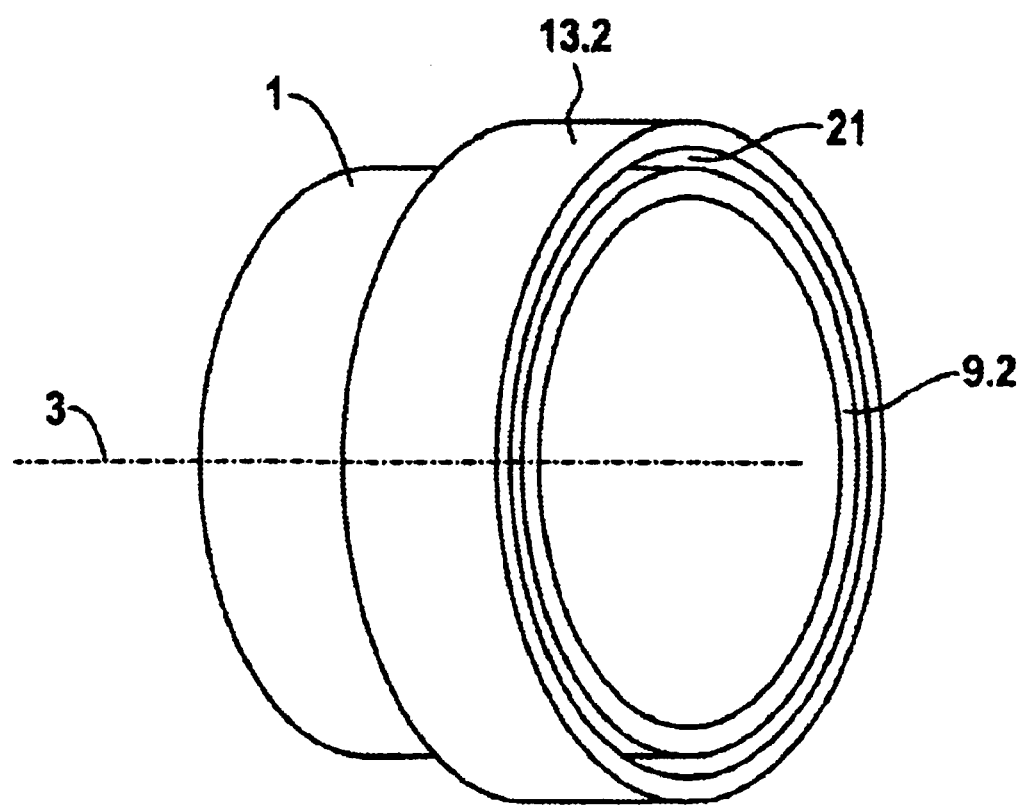

FIG. 4 shows an arrangement of a heat exchanger 9.2 offset axially in the direction of the rotational axis 3 relative to the gantry 1, a heat exchanger 13.2 being arranged around said heat exchanger 9.2.

The advantages of the invention are also effective in such modified arrangements of heal exchangers relative to one another as well as relative to the gantry 1, resulting in an improved elimination of the heat generated during operation of the X-ray source 2.

Although other modifications and changes may be suggested by those skilled in the art, it is the intention of the inventor to embody within the patent warranted hereon all changes and modifications as reasonably and properly come within the scope of their contribution to the art.

What is claimed is:

1. In an X-ray examination arrangement having an X-ray source mounted at a gantry which is rotatable around a rotational axis, the improvement of a cooling arrangement for said X-ray source comprising:

a first annular heat exchanger disposed at said gantry and in thermally conductive connection with said X-ray source, and rotatable around said rotational axis together with said gantry;

a second annular heat exchanger disposed in a thermally conductive, annular path with said first heat exchanger, with said first heat exchanger transferring heat from said X-ray source to said second heat exchanger directly via said annular path, said second heat exchanger being stationary relative to said first heat exchanger; and a plurality of inter-engaging annular guide devices for guiding an airstream, generated by rotation of said first heat exchanger and heated at said first heat exchanger, from said first heat exchanger to said second heat exchanger.

2. The improvement of claim 1 wherein said first heat exchanger comprises at least one heat exchange element.

3. The improvement of claim 1, wherein said first heat exchanger has a flow path therein, and further comprising a heat transfer medium flowing through said first heat exchanger in said flow path.

4. The improvement of claim 1 wherein said first heat exchanger comprises at least two heat exchange elements, and, further comprising a covering proceeding circumferentially around said rotational axis and disposed between said at least two heat exchange elements.

5. The improvement of claim 1, wherein said second heat exchanger is annularly disposed around said first heat exchanger.

6. The improvement of claim 1, wherein said second heat exchanger is disposed axially offset, along said rotational axis, from said first heat exchanger and is attached to said first heat exchanger.

7. The improvement of claim 1, wherein said second heat exchanger comprises at least one heat exchange element.

8. The improvement of claim 1, wherein said second heat exchanger comprises at least two annular heat exchange elements that are thermally conductively connected to each other.

9. The improvement of claim 8, further comprising a covering proceeding circumferentially around said rotational axis and disposed between said at least two heat exchange elements of said second heat exchanger.

10. The improvement of claim 1, wherein said second heat exchanger has a flow path therein, and further comprising a heat transfer medium flowing through said second heat exchanger in said flow path.

11. A computed tomography apparatus comprising:

a gantry rotatable around a rotational axis;

an X-ray source and an X-ray detector mounted opposite to each other on said gantry, said X-ray source emitting heat during operation thereof;

a first annular heat exchanger disposed at said gantry and rotatable with said gantry around said rotational axis, and having at least two heat exchange elements thermally conductively connected to each other, with at least one of said heat exchange elements being thermally conductively connected to said X-ray source for transferring said heat from said X-ray source;

a second heat exchanger disposed in a thermally conductive path relative to said first heat exchanger, with said first heat exchanger transferring heat from said X-ray source to said second heat exchanger directly via said thermally conductive path and said second heat exchanger transferring said heat transferred from said first heat exchanger to an exterior of said gantry; and a plurality of inter-engaging annular guide devices for guiding an airstream, generated by rotation of said first heat exchanger and heated at said first heat exchanger, from said first heat exchanger to said second heat exchanger.

12. A computed tomography apparatus comprising:

a gantry rotatable around a rotational axis;

an X-ray source and an X-ray detector mounted opposite to each other on said gantry, said X-ray source emitting heat during operation thereof;

a first annular heat exchanger disposed at said gantry and rotatable together with said gantry around said rotational axis, and thermally conductively connected to said X-ray source;

a second heat exchanger disposed in a thermally conductive path with said first heat exchanger, with said first heat exchanger transferring heat from said X-ray source to said second heat exchanger directly via said thermally conductive path, and said second heat exchanger being stationary relative to said first heat exchanger; and a plurality of inter-engaging annular guide devices for guiding an airstream, generated by rotation of said first heat exchanger and heated at said first heat exchanger, from said first heat exchanger to said second heat exchanger.

\* \* \* \* \*